United States Patent [19]

Hannart

[11] 4,002,633
[45] Jan. 11, 1977

[54] NOVEL COMPOUNDS: N-DISUBSTITUTED AMINO-ETHYL ESTERS OF RAUBASINE OF THE GENERAL FORMULA

[75] Inventor: Jean Alfred Alphonse Joseph Hannart, Brussels, Belgium

[73] Assignee: Omnium Chimique Societe Anonyme, Brussels, Belgium

[22] Filed: July 10, 1975

[21] Appl. No.: 594,875

[30] Foreign Application Priority Data

July 26, 1974 Belgium .............................. 818145

[52] U.S. Cl. .................... 260/293.53; 424/248.55; 424/250; 424/267; 260/247.2 B; 260/268 PC
[51] Int. Cl.² ........................................ C07D 471/04
[58] Field of Search .......... 260/247.2, 293.53, 268; 424/248, 250, 263, 267

[56] References Cited
UNITED STATES PATENTS 3,104,243  9/1963  Gillo ........................... 260/293.53
3,337,561  8/1967  Mueller ....................... 260/293.53

FOREIGN PATENTS OR APPLICATIONS 2,215,169  10/1972  Germany ...................... 260/293.53

Primary Examiner—John D. Randolph

[57] ABSTRACT

As novel compounds: N-disubstituted amino-ethyl esters of raubasine of the general formula:

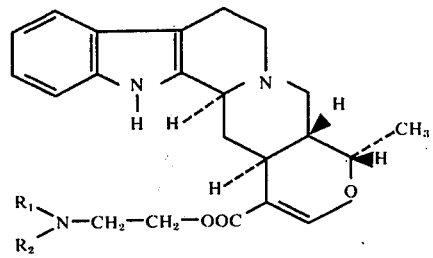

in which:

$R_1$ and $R_2$ are alkyl radicals or form together with the nitrogen atom to which they are attached a heterocyclic ring of the morpholinyl, piperidinyl, piperazinyl or pyrrolidinyl type.

Preparation of the compounds by reacting raubasinic acid with a halide of a substituted amino-ethane of the formula

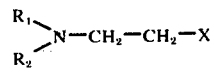

$R_1$ and $R_2$ have the same significance and X is a halogen in an organic solvent in the presence of an alkali carbonate insoluble in the reaction medium.

3 Claims, 1 Drawing Figure

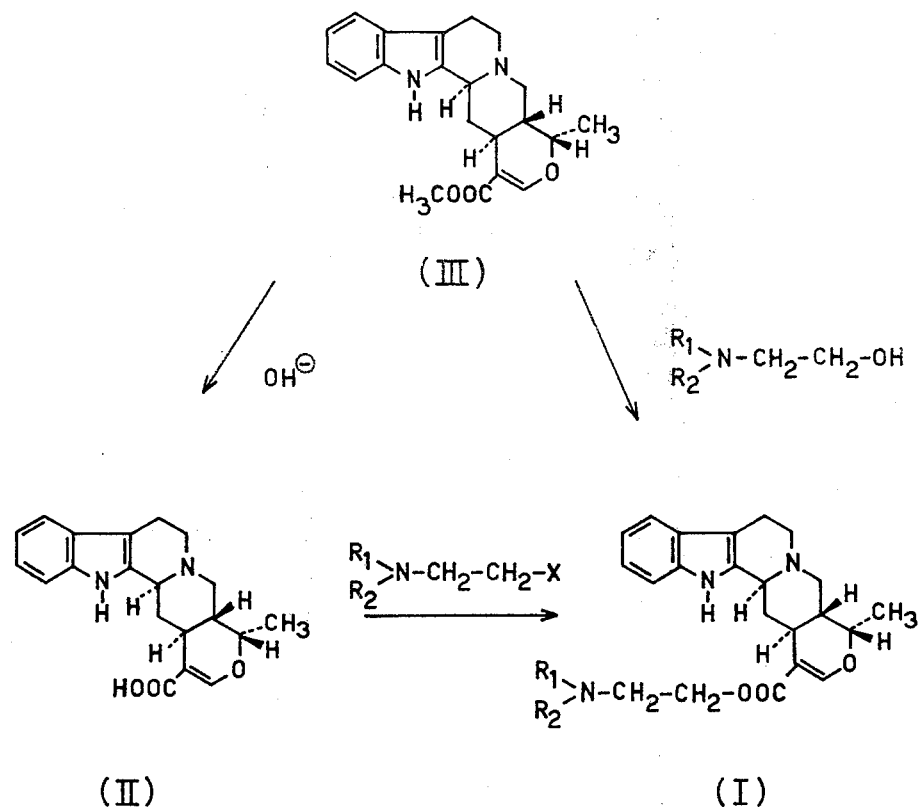

NOVEL COMPOUNDS: N-DISUBSTITUTED AMINO-ETHYL ESTERS OF RAUBASINE OF THE GENERAL FORMULA

The present invention has for its object novel compounds of N-disubstituted amino-ethyl esters or raubasine of the general formula (1)

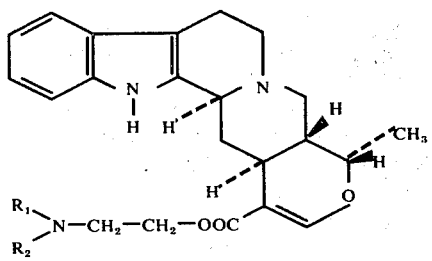

in which $R_1$ and $R_2$ are alkyl radicals or form together with the nitrogen atom to which they are attached, a heterocyclic ring preferably of the morpholinyl, piperidinyl, piperazinyl or pyrrolidinyl type.

These esters useful in therapeutics can be obtained by different processes.

The invention equally relates to the process for preparing them as well as to pharmaceutical compositions containing them.

The formulae are reproduced in the attached drawings which illustrate the reaction scheme of the different processes.

I. Preparation of the esters starting from raubasinic acid.

This procedure consists of reacting the raubasinic acid with a halide of a substituted amino ethane of the formula

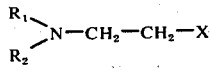

in which $R_1$ and $R_2$ have the above significance and X is a halogen in an organic solvent in the presence of an insoluble alkaline carbonate in the reaction mixture. The reaction is advantageously effected by heating the reactants under reflux preferably in an inert atmosphere.

As useful organic solvents, one can cite anhydrous alcohols and in particular isopropanol. All other organic solvents which do not dissolve alkaline carbonates can also be used.

The preferred alkali carbonate is sodium carbonate. It has for its aim to fix the halohydric acid HX liberated in the course of the reaction. This displaces the equilibrium in the desired sense and consequently increases the yield.

II. Preparation of the esters starting from raubasine by transesterification.

This method enables the esters to be obtained in a single stage with a good yield and a sufficiently short reaction time. The starting product is raubasine (III) and is reacted with an aminoalcohol of the formula

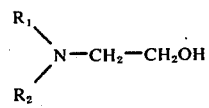

wherein $R_1$ and $R_2$ have the above indicated meanings. As catalyst one can employ an alkali metal alcoholate, preferably an alcoholate of an amino alcohol of the formula

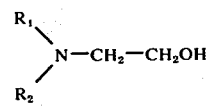

(one of the reactants) or sodium methylate. The solvent can be an aromatic hydrocarbon. The methanol, formed during the course of the reaction, can be eliminated by molecular sieves being given that the latter can absorb in general lower straight chain alcohols. The reaction is generally effected in an inert atmosphere. The product can be isolated by washing with water the organic phase in order to eliminate unreacted alcohol. The organic phase is then dried over sodium sulphate and distilled dry under vacuum. The residue thus obtained is dissolved in an organic solvent and treated with dried gaseous hydrochloric acid or concentrated hydrochloric acid to obtain the desired hydrochloride.

The following examples illustrate the non-limitative characteristics of the invention:

EXAMPLE 1

Hydrochloride of dimethylamino ethyl raubasinate.

A solution of 3.75 g of raubasinic acid hydrochloride in 100 ml of anhydrous isopropanol, in the presence of 2.12 g of anhydrous sodium carbonate is heated under reflux with agitation and under an atmosphere of nitrogen with 1.08 g of dimethylaminochlorethane.

After 4 hours, the mixture is filtered and the precipitate is washed with a little dry isopropanol. The alcoholic solution is evaporated, the residue is re-dissolved in 100 ml of methylene chloride washed in water and evaporated to dryness under vacuum. The residue is re-dissolved in isopropanol and acidified with hydrochloric acid. The crystals are filtered and recrystallised in methanol. One obtains 2.4 g of dimethylaminoethyl raubasinate hydrochloride.

Fusion: 291°–292° C $(\alpha)_D$: 0° (c = 0.5 $H_2O$)

U.V. spectrum: $\lambda$max m$\mu$ (log $\epsilon$): 222(4.87); 288 (4.22);

I.R. spectrum: ester carbonyl at 1695 cm$^{-1}$

N.M.R. spectrum:

a doublet of 3 protons centred at 1.18 a singlet of 6 protons at 2.46 a mass of 3 protons at 4.40 a mass of 5 protons between 7.10 and 7.70 a singlet of 1 proton at 8.63.

| Analysis : $C_{24}H_{31}N_3O_3$ . 2HCl | | | |
|---|---|---|---|
| | % C | % H | % N |
| Calculated | 59.75 | 6.87 | 8.71 |

-continued

Analysis : C₂₄H₃₁N₃O₃ . 2HCl

|  | % C | % H | % N |
|---|---|---|---|
| Found | 59.77 | 6.90 | 8.69 |

EXAMPLE 2

Hydrochloride of 1-methyl-4β piperazine raubasinate.

A solution of 3.75 g of raubasinic acid hydrochloride in 100 ml of anhydrous isopropanol in the presence of 3.20 g of anhydrous sodium carbonate is heated under reflux with agitation and in nitrogen atmosphere with 2.35 g of 1-methyl-4β chloroethylpiperazine dihydrochloride. After 4 hours the mixture is treated as in Example 1. One obtains 3.2 g of 1-methyl-4β ethylpiperazine raubasinate hydrochloride.

Fusion: 238°–240° C
$(\alpha)_D$: −6° (c = 0.4 H₂O)
U.V. spectrum: λmax mμ(log ε): 219 (4.43); 278 (3.82)
I.R. spectrum: ester carbonyl at 1710 cm⁻¹
N.M.R. spectrum:
a doublet of 3 protons centred at 0.90
a singlet of 3 protons at 2.11
a triplet of 2 protons at 4.20
a mass of 5 protons between 6.86 and 7.44
a singlet of 1 proton at 9.40

Analysis : C₂₇H₃₈N₄O₃ . 3HCl

|  | % C | % H | % N |
|---|---|---|---|
| Calculated | 56.50 | 6.85 | 9.76 |
| Found | 56.57 | 6.81 | 9.71 |

EXAMPLE 3

Hydrochloride of N-β ethyl pyrrolidine raubasinate.

To a solution of 1.16 g of pyrrolidino ethanol in 100 ml of dry benzene one adds 0.23 g of sodium. To the mixture obtained, one adds 3.52 g of raubasine and refluxes under an atmosphere of nitrogen and sheltered from the light for 4 hours. The mixture is then cooled and washed with water. The benzene phase is then dried on anhydrous sodium sulphate and distilled under vacuum. The residue is dissolved in isopropanol and acidified by gaseous hydrochloric acid. One obtains 3.74 g of N-β ethyl pyrrolidine raubasinate hydrochloride.

Fusion: 281°–283° C
$(\alpha)_D$: +16.2° (c = 0.4 .H₂O)
U.V. spectrum: λmax mμ (log ε): 225 (4.73; 236 (4.19)
I.R. spectrum: ester carbonyl at 1695 cm⁻¹
N.M.R. spectrum:
a doublet of 3 protons at 1.14
a quintuplet of 4 protons at 1.81
a triplet of 3 protons at 4.40
a mass of 5 protons between 7.00 and 7.70
a singlet of 1 proton at 8.63

Analysis : C₂₆H₃₃N₃O₃ . 2HCl

|  | % C | % H | % N |
|---|---|---|---|
| Calculated | 61.41 | 6.94 | 8.26 |
| Found | 61.50 | 6.90 | 8.25 |

EXAMPLE 4

Hydrochloride of N-β ethylmorpholine raubasinate.

To a solution of 1.32 g of morpholinethanol in 100 ml of dry benzene one adds 0.23 g of sodium. To the mixture obtained one adds 3.52 g of raubasine and refluxes under an atmosphere of nitrogen and sheltered from the light for 4 hours. The mixture is then treated as in Example 3. One obtains 3.93 g of N-β ethylmorpholine raubasinate hydrochloride.

Fusion: 235°–237° C
$(\alpha)_D$: −12.5° (c = 0.4. H₂O)
U.V. Spectrum: λmax mμ (log ε): 220 (4.56); 288 (3.70)
I.R. spectrum: ester carbonyl at 1695 cm⁻¹
N.M.R. spectrum:
a doublet of 3 protons at 1.13
a triplet of 4 protons at 3.73
a triplet of 3 protons at 4.31
a mass of 5 protons between 7.00 and 7.60
a singlet of 1 proton at 8.47

Analysis : C₂₆H₃₃N₃O₄ . 2HCl

|  | % C | % H | % N |
|---|---|---|---|
| Calculated | 59.54 | 6.73 | 8.01 |
| Found | 59.27 | 6.70 | 8.04 |

EXAMPLE 5

Hydrochloride of N-β ethyl piperidine raubasinate.

A solution of 3.1 g of raubasinic acid hydrochloride in 100 ml of anhydrous isopropanol in the presence of 1.6 g of anhydrous sodium carbonate is heated under reflux with agitation and under an atmosphere of nitrogen with 1.4 g of chloroethyl piperidine. After 3 hours under reflux the mixture is treated as in Example 1. One obtains 2.9 g of N-β ethylpiperidine raubasinate hydrochloride.

Fusion: 285°–286° C
$(\alpha)_D$: −17.5° (c = 1. H₂O)
U.V. spectrum: λmax mμ (log ε): 222 (4.74); 274 (3.77)
I.R. spectrum: ester carbonyl at 1715 cm⁻¹
N.M.R. spectrum:
a doublet of
 3 protons at 1.23
 6 protons at 1.53
a triplet of 2 protons at 4.33
a mass of 5 protons between 7.00 and 7.70
a singlet of 1 proton at 8.51

Analysis : C₂₇H₃₅N₃O₃ . 2HCl

|  | % C | % H | % N |
|---|---|---|---|
| Calculated | 62.06 | 7.14 | 8.04 |
| Found | 61.99 | 7.12 | 8.05 |

The esters of raubasine keep the adrenolytic properties of the molecule from which they are derivated, their toxicity being however less than that of raubasine.

In the cardiovascular field, the action of these new products is characterised by a substantial increase of blood flow and a decrease of the peripheral circulatory resistance, without hypotension. Having much less tachycardiac properties than raubasine, the esters according to this invention have, in addition, a notable cardio-analeptic effect. Their duration of action is also longer than that of raubasine. Cardiac insufficiencies, shock conditions, insufficiencies of peripheral and cerebral blood circulation, artery troubles are successfully treated.

Examples of compositions:

Pill

-continued

Examples of compositions:

| Raubasine ester | 0.025 g |
| Sucrose | |
| Magnesium stearate | to make one pill of |
| Dye | 0.350 g |
| Talc | |
| Starch | |

Capsule
| Raubasine ester | 0.025 g |
| Lactose | to make one capsule of 120 mg |

The daily doses vary between 50 and 100 mg i.e. 2 to 4 pills or capsules to be administered orally.

What I claim is:
1. N-β-ethylpiperidine raubasinate.
2. The compound of claim 1 in the form of an acid addition salt.
3. The compound of claim 1 in the form of an hydrochloride.

* * * * *